(12) United States Patent
Yeung

(10) Patent No.: US 6,527,553 B2
(45) Date of Patent: Mar. 4, 2003

(54) DENTAL PROSTHESIS

(76) Inventor: Jean-Claude Yeung, 41, rue de Verun, 94220 Charenton le Pont (FR)

( * ) Notice: Subject to any disclaimer, the term of this patent is extended or adjusted under 35 U.S.C. 154(b) by 0 days.

(21) Appl. No.: 09/822,314

(22) Filed: Apr. 2, 2001

(65) Prior Publication Data

US 2001/0055743 A1 Dec. 27, 2001

(30) Foreign Application Priority Data

Mar. 31, 2000 (FR) .................................. 00 04144

(51) Int. Cl.⁷ .................................................. A61C 8/00
(52) U.S. Cl. ...................................................... 433/173
(58) Field of Search ............................... 433/172, 173, 433/174, 175, 176

(56) References Cited

U.S. PATENT DOCUMENTS

| | | | |
|---|---|---|---|
| 5,052,929 A | 10/1991 | Seal | 433/173 |
| 5,316,477 A | * 5/1994 | Calderon | 433/173 |
| 5,662,474 A | 9/1997 | Jorneus et al. | 433/172 |
| 5,674,072 A | * 10/1997 | Moser et al. | 433/173 |
| 5,695,337 A | 12/1997 | Tyszblat Sadoun | 433/173 |
| 5,947,732 A | * 9/1999 | Beaty et al. | 433/172 |

FOREIGN PATENT DOCUMENTS

| | | |
|---|---|---|
| EP | 0 473 262 | 3/1992 |
| WO | WO 96/25895 | 8/1996 |
| WO | WO 97/14372 | 4/1997 |

\* cited by examiner

*Primary Examiner*—Cary E. O'Connor
(74) *Attorney, Agent, or Firm*—Young & Thompson

(57) ABSTRACT

The invention relates to a prosthetic assembly comprising a pillar that is to receive a crown or a bridge, and a pillar screw for joining the pillar to an implant implanted in the patient's jawbone, the pillar screw comprising a body that can be joined to the implant and a head that interacts with the pillar. According to the invention, the head of the pillar screw is arranged in such a way that it projects from the patient's gum and forms with the pillar, through complementarity of shapes, a single volume that is to receive the crown or bridge, the pillar representing at least about half of the single volume.

15 Claims, 2 Drawing Sheets

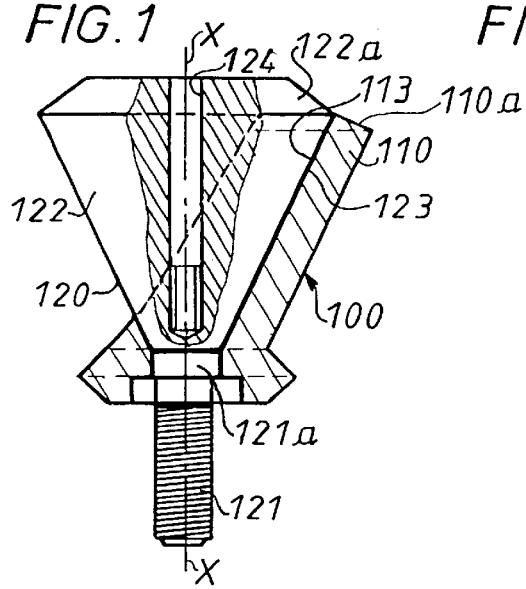
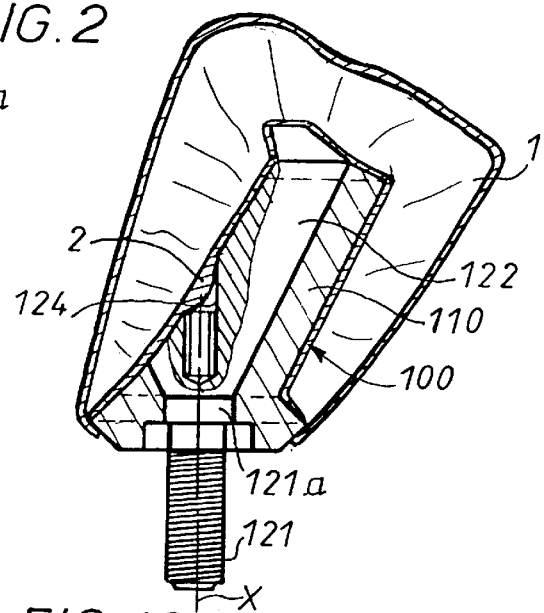
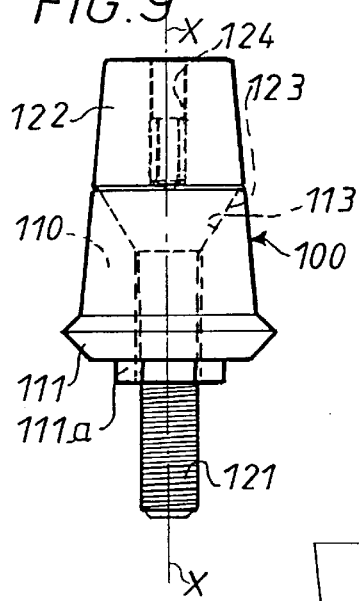
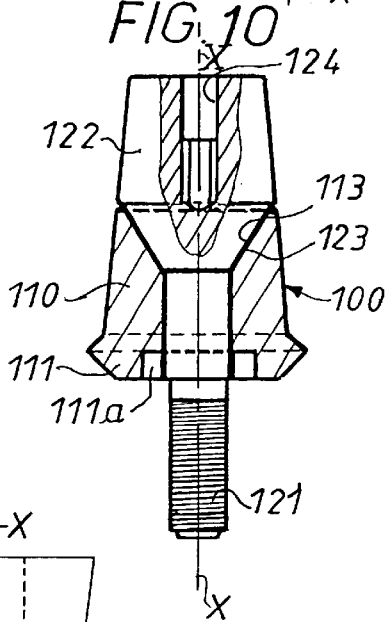
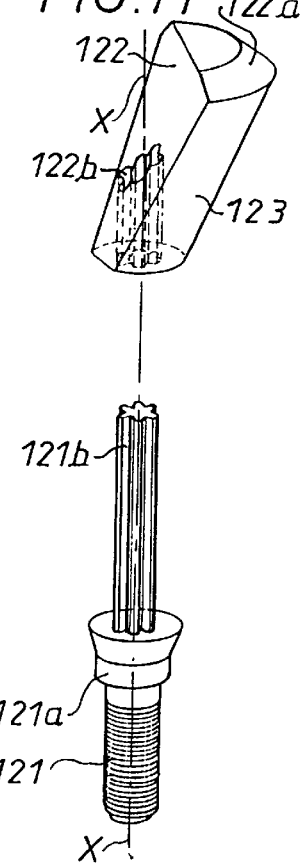
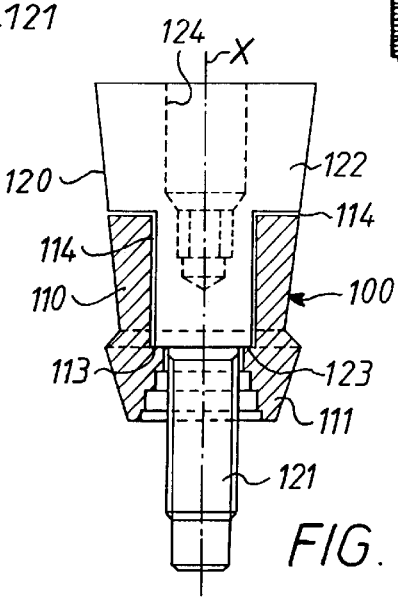

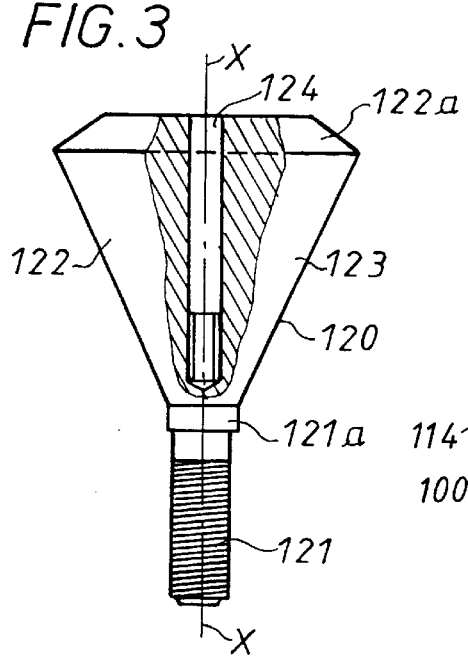
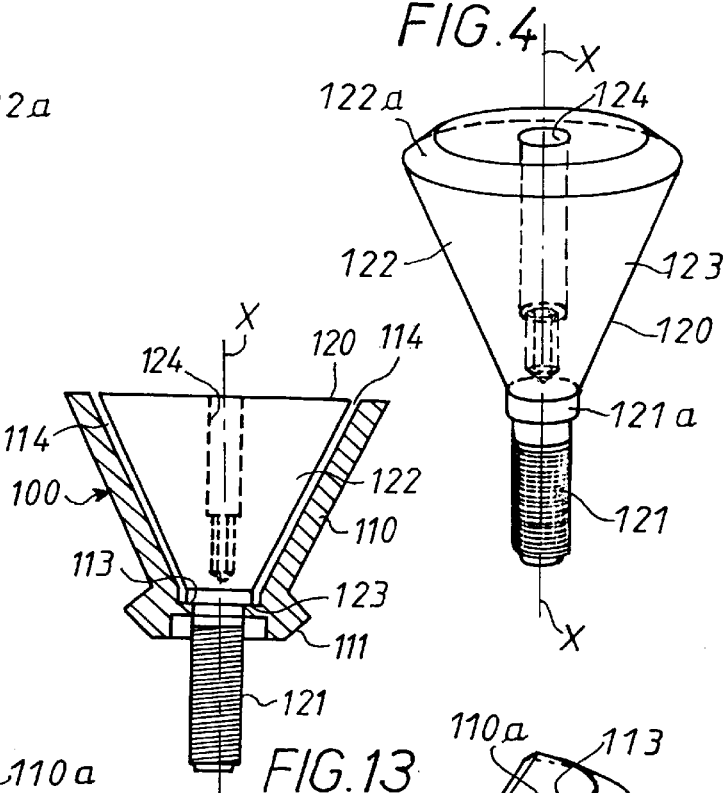
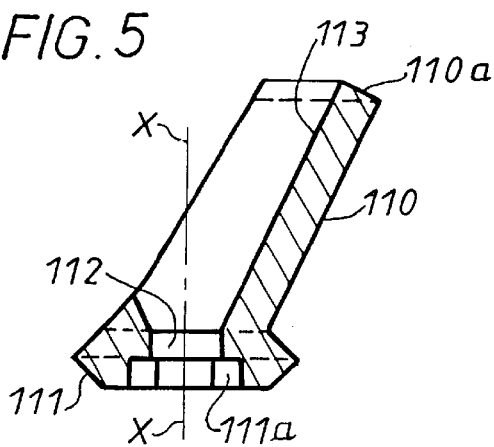
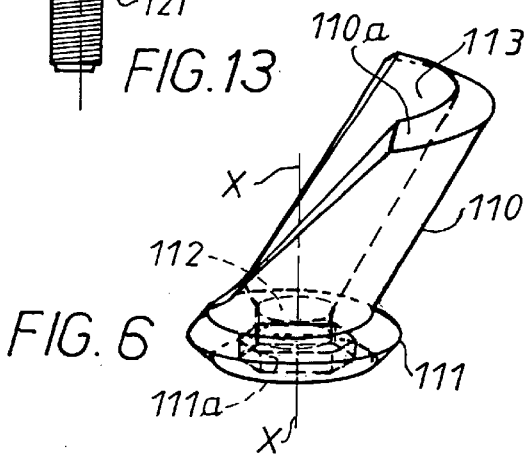
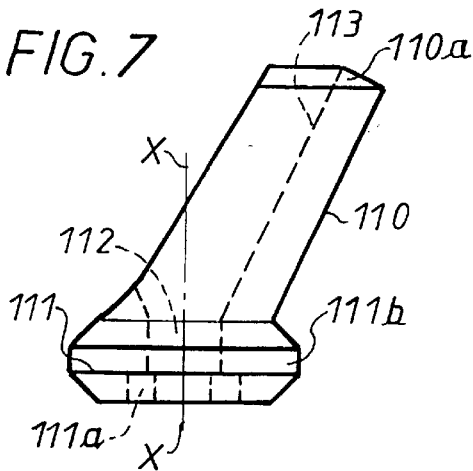
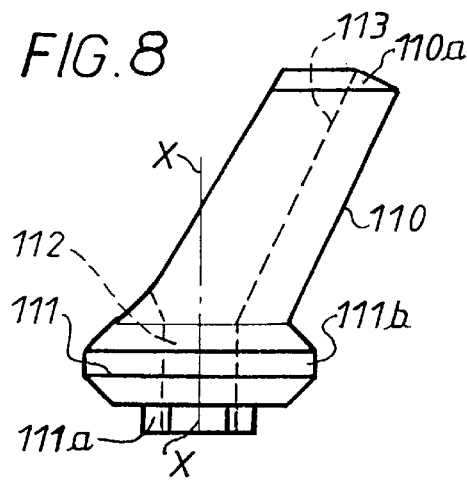

DENTAL PROSTHESIS

BACKGROUND OF THE INVENTION

1. Field of the Invention

The present invention relates in general to dental prostheses, and more particularly to a prosthetic assembly comprising a pillar intended to receive a crown or a bridge, and a pillar screw for joining the pillar to an implant implanted in the patient's jawbone, the said pillar screw comprising a body that can be joined to the implant and a head arranged so as to project from the patient's gum and form, in conjunction with the pillar, through complementarity of shapes, a single volume that is intended to receive the crown or the bridge.

2. Description of the Prior Art

In general, the pillar has a bottom end that is adapted on the one hand to the configuration of the implant to which it is joined, and on the other hand to the head of the pillar screw with which it interacts.

In fact, the implant can assume all kinds of configurations, such as an internal or external hexagon, or an internal or external octagon, or a cylinder provided with external or internal grooves. The implant can also have, in its inside wall, vertical grooves, in particular three vertical grooves arranged, when viewed in cross-section, at the vertices of a triangle, and the pillar then has, at its bottom end, corresponding vertical ribs that are intended to engage in the said grooves.

Furthermore, usually the pillar screw has a threaded body and passes through the bottom end of the pillar and screws into the body of the implant, thereby fixing the pillar on the implant.

The head of the pillar screw interacts with the bottom end of the pillar situated in the patient's gum so that the pillar screw and the pillar form an integral assembly fixed in the implant. The said head is generally cylindrical and is located inside the internal diameter of the pillar. Between the head of the screw and the pillar there is a lateral clearance to enable the said head to slide, the external surface of the pillar being alone in relation to and cemented to the inside surface of the prosthesis.

The difficulty with a prosthetic assembly of this kind is long-term maintenance of fixing of the pillar, by means of the pillar screw, on the implant.

In fact, after a certain length of time during which the dental prosthesis is regularly subjected to the stresses of chewing for example, it may be found that the fixation of the pillar screw in the implant has deteriorated and that some clearance has appeared between the pillar screw and the implant, consequently causing an equivalent looseness of the pillar carrying the crown or bridge relative to the implant, which is unacceptable.

Various solutions have already been proposed for avoiding this problem.

Among these solutions, we may cite the use of a pillar screw made of gold, which acts on the inside walls of the implant as a lubricant, reducing the friction between the thread of the said screw and that of the implant, which has the beneficial effect of increasing the tightening torque between the screw and the implant.

However, the use of pillar screws in twenty-four carat gold is by no means economical.

Another solution consists of providing an interaction of surfaces called a Morse taper between the head of the pillar screw and the bottom end of the said pillar, forming an anti-unscrewing system.

This interaction of tapered surfaces requires a special conformation of the internal and external surfaces of the head of the pillar screw and of the pillar, which is relatively complex.

Furthermore, these solutions cannot guarantee a reliable result.

Document WO 97/14372 describes such a solution in which the screw head has two parts, with one part extending inside the pillar and forming anti-rotating means with the latter, through interaction of tapered internal surfaces having the same angle. The second part of the screw head extends above the pillar and has grooves or flats that are intended to interact with the prosthesis to prevent it turning relative to the prosthetic assembly.

However, in the solution according to this document WO 97/14372, the part of the pillar that projects from the gum is very short and represents a small part of the single volume formed through the interaction of the screw head and the pillar. Thus, this projecting part of the pillar represents a very small supporting surface for the crown or bridge, and the prominent part that will mainly interact with the crown to hold it in place on the prosthetic assembly, whether in rotation or in axial translation, is formed by the head of the screw.

The short pillars of the aforementioned type are difficult to position because, with the head of the implant being located under the gum, they do not remain stationary during tightening of the pillar screw, but tend to turn in the sense of rotation of the screw. Moreover, it is necessary to use a controlled-torque contra-angle attachment, which increases the cost, the complexity and the force exerted on the implant.

In this context, the present invention proposes a new solution, which is simple and economical, for reinforcing the mechanical retention of the pillar screw in a dental implant.

SUMMARY OF THE INVENTION

More particularly, the invention proposes a prosthetic assembly comprising a pillar that is intended to receive a crown or bridge, and a pillar screw for joining the pillar to an implant implanted in a patient's jawbone, the said pillar screw comprising a body that can be joined to the implant and a head arranged so as to project from the patient's gum and interact with the pillar to form, through complementarity of shapes, a single volume that is to receive the crown or bridge. It is characterized in that the pillar represents at least about half of the said single volume in such a way that the external surfaces of the pillar and of the head of the pillar screw are able to be adapted to the internal surface of the crown or bridge to form anti-rotation surfaces of the said crown or bridge.

Thus, according to the invention, advantageously, the head of the pillar screw and the pillar are joined to one another by the adhesive cement permitting fixing of the crown or bridge on the said pillar, which makes it possible to reinforce the fixing of the said pillar screw in the implant and avoid any subsequent inopportune separation.

Other advantageous, non-limiting characteristics of the prosthetic assembly according to the invention are as follows:

the initial volume formed by the head of the pillar screw interacting with the pillar is greater than the final volume for receiving the crown or bridge, it being possible for the said head and/or pillar to be milled by the practitioner to adjust their shape to the final volume desired;

the pillar has an internal structure adapted to the external shape of the head of the pillar screw so that the said head and the said pillar comprise complementary supporting zones;

the complementary supporting zones of the head of the pillar screw and of the pillar are flat surfaces or portions of conical surfaces or cylindrical surfaces;

the head of the pillar screw has at its base, roughly at the junction with its body, a supporting surface that is to bear on a complementary supporting surface of the pillar provided just above its bottom end and intended to interact with the implant, moreover with a clearance between the screw head and the pillar;

the pillar screw is made in two separate parts, the body and the head, assembled together by an anti-rotation means which is preferably achieved through interaction of shapes between the two parts;

the head of the pillar screw has a roughly conical or cylindrical shape;

the pillar screw is made of pure titanium or of titanium alloy, or of gold alloy;

the pillar is made of pure titanium or of titanium alloy or of ceramic or of sinterable material.

The description that follows, referring to the appended drawings, given as non-limiting examples, will explain the essence of the invention and how it can be carried out.

BRIEF DESCRIPTION OF THE DRAWINGS

FIG. 1 is a view in axial section of a first embodiment of a prosthetic assembly according to the invention, the head of the pillar screw only being partially cut at the level of its channel for insertion of a control device (manipulator).

FIG. 2 shows the prosthetic assembly shown in FIG. 1, with a crown or bridge fitted thereon.

FIG. 3 shows the pillar screw of the prosthetic assembly shown in FIG. 1.

FIG. 4 is a perspective view of the pillar screw shown in FIG. 3.

FIG. 5 is a sectional view of the pillar shown in FIG. 1.

FIG. 6 is a perspective view of the pillar shown in FIG. 5.

FIG. 7 is a front view of a second embodiment of the pillar of the prosthetic assembly according to the invention.

FIG. 8 is a front view of a third embodiment of the pillar of the prosthetic assembly according to the invention.

FIGS. 9 and 10 are, respectively, front and axial sectional views of another embodiment of the prosthetic assembly according to the invention.

FIG. 11 is a schematic perspective view of a variant of the pillar screw of the prosthetic assembly according to the invention.

FIG. 12 is a partially-sectioned schematic view of another variant of the pillar screw and of the pillar of the prosthetic assembly according to the invention.

FIG. 13 is a partially-sectioned schematic view of another variant of the pillar screw and of the pillar of the prosthetic assembly according to the invention.

DETAILED DESCRIPTION OF THE PREFERRED EMBODIMENTS

Firstly, it is to be noted that from one embodiment to another shown in the various diagrams, identical or similar elements will as far as possible be given the same reference symbols and will not be described each time.

Referring first of all to FIGS. 1 to 8, a prosthetic assembly 100 is shown, comprising a pillar 110 that is to receive a crown or bridge 1. The crown or bridge 1 is joined to pillar 110 by adhesive or cement 2. The prosthetic assembly 100 also comprises a pillar screw 120 passing through the bottom end 111 of pillar 110, via a channel 112 provided in the bottom end 111 of the said pillar 110, for joining pillar 110 to an implant (not shown) implanted in the patient's jawbone.

According to the embodiment shown in FIGS. 1 to 4, the said pillar screw 120 generally extends along an axis X and comprises a body 121 which is overall a cylinder of revolution about axis X and is provided on part of its length with a thread that is intended to interact with a corresponding internal thread provided on the inside wall of the implant (not shown). In its upper part, body 121 of pillar screw 120 has a non-threaded part 121a that is intended to interact with an internal seating 112 provided in the bottom end 111 of pillar 110, this internal seating 112 forming a channel for pillar screw 120 and having a shape that complements the shape of the upper end 121a of body 121 of the said pillar screw 120.

Here, the top end 121a of body 121 of pillar screw 120 has a simple shape of a cylindrical crown of revolution, and the corresponding internal seating 112 in pillar 110 has a complementary shape of a cylinder of revolution about axis X, though it would of course be possible to provide any other complementary shape of the hexagon, octagon or other type.

The pillar screw 120 also has a head 122 that interacts with pillar 110.

According to the embodiment represented in FIGS. 1 to 4, the head 122 and the body 121 of pillar screw 120 form a single piece.

Advantageously, the head 122 of pillar screw 120 is arranged so as to project from the patient's gum, forming with pillar 110, through complementarity of shapes, a single volume for receiving the crown or bridge 1 (see FIG. 2).

This single volume is formed here advantageously largely by the pillar 110 which represents at least about half of the latter so that the external surfaces (not referenced) of head 122 of screw 120 and of pillar 110 are able to be adapted to the internal surface of the crown or bridge 1 to form anti-rotation surfaces of the said crown or bridge.

Thus, during fitting of the crown or bridge on the single volume formed by screw head 122 and pillar 110, the assembly is joined by the adhesive or the adhesive cement 2 necessary for joining the crown or bridge, and pillar screw 120 is finally locked against rotation inside the implant (not shown). This makes it possible to reinforce the fixing by screwing the body 121 of the screw in the implant.

The initial volume formed by the head 122 of the pillar screw 120 interacting with pillar 110 is larger than the final volume for receiving the crown or bridge (see FIGS. 1 and 2). The head 122 and/or the pillar 110 can then be milled by the practitioner to adapt their shape to the final volume desired.

After this milling of head 122 of screw 120 and/or of pillar 110, the proportion of the single volume constituted by pillar 110 is further accentuated and can represent practically two-thirds of the said single volume.

Pillar 110 has an internal structure that is adapted to the external shape of head 122 of pillar screw 120, so that the said head 122 of pillar screw 120 and the pillar 110 comprise complementary supporting zones 123 and 113.

According to the embodiment represented in FIGS. 1 to 8, the complementary supporting zones 123 and 113 of head 122 of pillar screw 120 and of pillar 110 are portions of conical surfaces.

For this purpose, head 122 of pillar screw 120 in this case has a conical shape, and the pillar is "pre-angled", i.e. it generally extends in a direction forming an angle with axis X, and it has an internal surface in the form of a portion of a cone (see more especially FIG. 6). Such a pillar can be "pre-angled" with different angles during machining or alternatively it can have an initial volume larger than the final volume, with the intention that this initial volume is milled to give a desirable orientation relative to the axis of insertion of the crown or bridge. The tapered upper surface 122a of head 122 of pillar screw 120 is a continuous extension of the tapered upper surface 110a of pillar 110.

Of course, as will be explained in more detail with reference to FIGS. 9 and 10, the head 122 of pillar screw 120 and the pillar 110 can have other forms, in particular the head 122 of the pillar screw can be of inverted cone shape, cylindrical or stepped cylindrical, increasing in volume towards its top. Pillar 110 can also have a slightly conical shape extending along axis X, as shown more especially in FIGS. 9 and 10.

As shown more particularly in FIGS. 1 to 4, head 122 of pillar screw 120 has an axial channel 124 for the introduction of a manipulator permitting its introduction through pillar 110 and its screwing inside the implant (not shown). This axial channel 124 has a length such that once the head 122 of pillar screw 120 is taken back by milling, a portion of channel 124 remains accessible to the manipulator for possible unscrewing of the screw if necessary.

FIGS. 9 and 10 show another embodiment of the prosthetic assembly 100 according to the invention, wherein the pillar 110 has an overall conical shape extending along axis X of pillar screw 120, and the head 122 of the pillar screw introduced through pillar 110 also has an overall conical complementary shape. The head 122 forms an extension along axis X of pillar 110. The complementary supporting zones 123 and 113 of head 122 of pillar screw 120 and of pillar 110 are also in this case portions of conical surfaces, but it could be envisaged, in a variant that is not shown, that these complementary supporting surfaces should be cylindrical surfaces or alternatively flat surfaces.

Once again, the head 122 of pillar screw 120 and/or the pillar 110 can be milled back by the practitioner to adapt their shape to the desired final volume for receiving the crown or bridge.

According to the embodiment represented in FIGS. 9 and 10, the body 121 of pillar screw 120 has a larger non-threaded part passing through pillar 110.

According to the embodiment represented in FIG. 12, the head 122 of pillar screw 120 has at its base, roughly at the junction with its body 121, a supporting surface 123, in this instance a flat surface, intended to bear on a flat complementary supporting surface 113 of pillar 110 provided just above its bottom end 111 that is to interact with the implant, moreover with a clearance 114 between head 122 of pillar screw 120 and the pillar 110.

The complementary supporting surfaces of the head of the pillar screw and of the pillar can also be conical or cylindrical-conical surfaces.

FIG. 13 shows a variant embodiment wherein the head 122 of pillar screw 120 has a conical shape, and pillar 110 also has a conical shape that envelops the head 122 of pillar screw 120.

The head 122 of pillar screw 120 also has at its base, roughly at the junction with its body 121, a flat supporting surface 123 (which can be conical or cylindrical-conical) intended to be supported on a flat (or conical or cylindrical-conical) complementary supporting surface 113 of pillar 110 provided just above its bottom end 111 intended to interact with the implant, moreover there is a clearance 114 between head 122 of pillar screw 120 and the pillar 110.

The practitioner can work by milling the large volume represented by the head 122 of pillar screw 120 and the pillar 110, to adjust the external surfaces of head 122 and of pillar 110 to the inside surface of the crown or bridge 1 (see FIG. 2) so that the latter form anti-rotating or anti-rotational surfaces of the said crown 1 fitted on the machined single volume.

In particular, the practitioner can at his discretion "pre-angle" the pillar 110 by milling, to arrive at a configuration similar to that shown in FIG. 1.

FIG. 11 shows another embodiment of pillar screw 120 of the prosthetic assembly 100 of the invention, according to which the said pillar screw 120 is constructed of two separate parts, the body 121 and the head 122, assembled together by an anti-rotating means 121b, 122b.

The anti-rotating means 121b, 122b is produced by an interaction of forms between the two parts 121, 122. Here, the body 121 of pillar screw 120 has, above its threaded part, a rod or stub extending along axis X and having, on its external surface, flutes 121b that interact with the complementary grooves 122b of an internal axial tube provided in the head 122 of pillar screw 120.

Of course, in addition, the two parts 121, 122 of pillar screw 120 are assembled together axially by means of cement or adhesive placed at the base of each of the two parts.

With regard to the anti-rotating means, according to other variants that are not shown it is possible to envisage any other complementary shape such as a hexagonal, octagonal, square or even elliptical shape.

With regard more particularly to pillar 110 of prosthetic assembly 100, as shown in the various diagrams, and especially in FIGS. 5 to 8, the latter has a bottom end 111, 111a adapted to all kinds of implant configurations, such as a configuration as an external or internal hexagon, or as an external or internal octagon (see FIGS. 5 to 8), or alternatively to a cylindrical configuration with external or internal grooves. It is also possible to envisage an implant that has an external or internal hexagonal end configuration and a pillar where the configuration of its bottom end interacting with the implant is dodecagonal, so that it permits positioning of the pillar relative to the implant in twelve different positions.

Such a pillar can have a bottom end of different heights so that it can be adapted to gums of different thicknesses. In particular, the pillar shown in FIGS. 7 and 8 has, relative to that shown in FIGS. 5 and 6, a larger base height, provided by an overthickness 111b between the upper part and the lower part of the bottom end 111 of the said pillar.

Moreover, such a pillar, with a large external surface adapted to interact with the internal surface of a prosthetic element, can have arrangements that increase its retention with a prosthetic element, such as vertical or horizontal grooves, special surface treatment, transverse holes or other arrangements. It can receive extension rings made of various materials, for example titanium, ceramics or others. The said pillar can also have at its base, where it supports the pillar screw, a variable shape that can be flat or conical.

Finally, the pillar, which is generally cylindrical at the level of encirclement of the gum, can be anatomical, i.e. its cross-section can be that of a natural root.

The pillar screw 120 is preferably made of pure titanium, of titanium alloy, or of gold alloy.

When it is made in two parts, the first part constituting the screw body can be made of titanium alloy, of pure titanium, of gold or of any other suitable material. The second part can be made of titanium alloy, of pure titanium, of sinterable material, of ceramic or of any other suitable material.

The pillar 110 of the prosthetic assembly is preferably made of pure titanium or of titanium alloy, or of ceramic or of sinterable material.

The present invention is by no means limited to the embodiments that have been described and illustrated, but a person skilled in the art will be able to introduce any variant within the spirit of the invention.

There is claimed:

1. A prosthetic assembly comprising a pillar that is to receive a crown or a bridge, and a pillar screw for joining the pillar to an implant implanted in the patient's jawbone, the said pillar screw comprising a body that can be joined to the implant and a head having an external surface and being arranged so as to project from the patient's gum and interact with the pillar to form, through complementarity of shapes, a single volume that is to receive the crown or bridge, wherein the pillar has an external surface that represents at least about half of the said single volume so that when the pillar and the pillar screw are assembled, the external surfaces of the pillar and of the head of the pillar screw interact with each other so that at least a part of the external surface of the head of the pillar screw is situated outside the pillar to form with the external surface of the pillar a single external surface which is adapted to the inside surface of the crown or bridge to form an anti-rotational surface of the said crown or bridge.

2. A prosthetic assembly according to claim 1 wherein the initial volume formed by head of pillar screw interacting with pillar is larger than the final volume for receiving the crown or bridge, it being possible for the said head and/or the pillar to be milled by the practitioner in order to adapt their shape to the desired final volume.

3. A prosthetic assembly according to claim 1 wherein the pillar has an internal structure that is adapted to the external shape of the head of pillar screw in such a way that the said head and the said pillar include complementary supporting zones.

4. A prosthetic assembly according to claim 3 wherein the complementary supporting zones of the head of pillar screw and of pillar are flat surfaces.

5. A prosthetic assembly according to claim 4 wherein the head of pillar screw has at its base, roughly at the junction with its body, a supporting surface that is intended to bear upon a complementary supporting surface of pillar provided just above its bottom end that is intended to interact with the implant, there being moreover a clearance between the head of pillar screw and the pillar.

6. A prosthetic assembly according to claim 3 wherein the complementary supporting zones of head of pillar screw and of pillar are portions of conical surfaces.

7. A prosthetic assembly according to claim 3 wherein the complementary supporting zones of the head of the pillar screw and of the pillar are cylindrical surfaces.

8. A prosthetic assembly according to claim 3 wherein the head of pillar screw has at its base, roughly at the junction with its body, a supporting surface that is intended to bear upon a complementary supporting surface of pillar provided just above its bottom end that is intended to interact with the implant, there being moreover a clearance between the head of pillar screw and the pillar.

9. A prosthetic assembly according to claim 1 wherein the pillar screw is made of two separate parts, the body and the head, assembled together by an anti-rotating means.

10. A prosthetic assembly according to claim 9 wherein the said anti-rotating means is achieved through interaction of shapes between the two parts.

11. A prosthetic assembly according to claim 1 wherein the head of pillar screw has a shape that is approximately conical or cylindrical.

12. A prosthetic assembly according to claim 1 wherein the pillar screw is made of pure titanium or of titanium alloy.

13. A prosthetic assembly according to claim 1 wherein the pillar screw is made of gold alloy.

14. A prosthetic assembly according to claim 1 wherein the pillar is made of pure titanium or of titanium alloy.

15. A prosthetic assembly according to claim 1 wherein the pillar is made of ceramic or of a sinterable material.

* * * * *